US006543456B1

(12) United States Patent
Freeman (10) Patent No.: US 6,543,456 B1
(45) Date of Patent: Apr. 8, 2003

(54) METHOD FOR MINIMALLY INVASIVE SURGERY IN THE DIGESTIVE SYSTEM

(75) Inventor: Lynetta J. Freeman, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 10/159,054

(22) Filed: May 31, 2002

(51) Int. Cl.$^7$ .............................................. A61B 19/00
(52) U.S. Cl. ....................................... 128/898
(58) Field of Search ......................... 128/898

(56) References Cited

U.S. PATENT DOCUMENTS

| | | |
|---|---|---|
| 5,197,649 A | 3/1993 | Bessler et al. |
| 5,411,508 A | 5/1995 | Bessler et al. |
| 6,279,809 B1 | 8/2001 | Nicolo |

FOREIGN PATENT DOCUMENTS

| | | |
|---|---|---|
| EP | 0 540 010 A2 | 5/1993 |
| WO | WO 00/72765 A1 | 12/2000 |
| WO | WO 01/62162 A1 | 8/2001 |
| WO | WO 01/62163 A1 | 8/2001 |
| WO | WO 01/62164 A2 | 8/2001 |
| WO | WO 01/66020 A2 | 9/2001 |

OTHER PUBLICATIONS

Alternative Operative Techniques in Laparoscopic Roux–en–Y Gastric Bypass for Morbid Obesity, Borao et al. JSJS (2001) 5:123–129.

Laparoscopic Roux–en–Y Gastric Bypass: Transoral or Transgastric Anvil Placement? Scott et al. Obesity Surgery, 10, 361–365.

Laparoscopic Gastric Bypass: Roux–en–Y Gastric Bypass—500 Patients: Techniques and Results, with 3–60 month follow–up, Wittgrove et al., Obesity Surgery, 10, 233–239.

Laparoscopic Gastric Bypass: Roux–en–Y–Preliminary Report of Five Cases, Wittgrove et al., Obesity Surgery, 4, 353–357.

Correspondence: Laparoscopic Gastric Bypass: Endostapler Transoral or Transabdominal Anvil Placement, Wittgrove et al., Obesity Surgery, 10, 376–377.

Website: www.pmi2.com.

Sales Brochure from Power Medical Interventions.

*Primary Examiner*—Corrine McDermott
*Assistant Examiner*—William H Matthews

(57) ABSTRACT

A method for intraluminally performing a gastric bypass surgery is provided. Two anastomosis members are inserted transorally and located in a proximal position and a distal position within the digestive system. The stomach and the small intestine are transected to create a gastric pouch, a drainage loop, and a Roux limb. The distal anastomosis member joins the drainage loop to a distal portion of the intestine, and the proximal anastomosis member joins the Roux limb to the gastric pouch.

21 Claims, 7 Drawing Sheets

METHOD FOR MINIMALLY INVASIVE SURGERY IN THE DIGESTIVE SYSTEM

FIELD OF THE INVENTION

The present invention relates, in general, to surgery and, more particularly, to a method of performing a surgical procedure on the digestive system.

BACKGROUND OF THE INVENTION

The percentage of the world population suffering from morbid obesity is steadily increasing. Severely obese persons are susceptible to increased risk of heart disease, stroke, diabetes, pulmonary disease, and accidents. Because of the effect of morbid obesity to the life of the patient, methods of treating morbid obesity are being researched.

Numerous non-operative therapies for morbid obesity have been tried with virtually no permanent success. Dietary counseling, behavior modification, wiring a patient's jaws shut, and pharmacologic methods have all been tried, and, though temporarily effective, failed to correct the condition. Nonsurgical approaches using mechanical devices, such as esophago-gastric balloons to fill the stomach have also been used to treat the condition. Such devices cannot be employed over a long term, however, as they often cause severe irritation, necessitating their periodic removal and hence interruption of treatment. Thus, the medical community has evolved surgical approaches to treatment of morbid obesity. Many surgical procedures for treatment of morbid obesity may generally be classified as being directed toward creation of a smaller stomach, also known as gastro-restrictive surgery, or toward the prevention of absorption of food, the most common of which is the gastric bypass. In variations of the gastric bypass, the stomach is divided into two pouches, with the upper pouch connected to the esophagus and having a small food capacity. The lower pouch remains in situ connected to the duodenum. The upper pouch is then surgically attached to a portion of the small intestine, called the jejunum, through a small opening. The opening restricts the passage of food by the greatly reduced useable stomach. The smaller stomach causes a feeling of fullness, or early satiety, with less food consumption, causing the patient to eat less food overall.

Minimally invasive methods to perform gastric bypass have been developed. These methods can involve five to seven laparoscopic ports inserted into the abdominal cavity. Instruments are used through the ports to create a small gastric pouch to restrict food intake and to bypass a portion of the intestine to cause malabsorption of ingesta. The procedure is described in Wittgrove, Alan C., MD, Clark, G. Wesley, MD, and Tremblay, Laurier J. MD *Laparoscopic Gastric Bypass, Roux-en-Y: Preliminary Report of Five Cases, Obesity Surgery*, Volume 4, Number 4 (November, 1994), pp. 353–357. In the procedure, a gastric pouch is formed by dissecting the stomach. Repeated applications of an endoscopic linear cutter are used to separate a small portion of the stomach just distal to the esophagus from the rest of the stomach. The jejunum is then transected distally with a linear stapler. (An example of a linear stapler can be found in U.S. Pat. No. 5,673,840, issued on Oct. 7, 1997 which is hereby incorporated herein by reference.) Thereafter, the distal portion of the jejunum, called the Roux-limb, is brought to form an anastomosis with the gastric pouch, often referred to as a gastroenterostomy. The gastroenterostomy can be performed with a linear stapler, circular stapler, or hand sewing. (An example of a circular stapler can be found in U.S. Pat. No. 5,104,025 issued on Apr. 14, 1992, which is hereby incorporated herein by reference.) Following the gastroenterostomy, a side to side anastomosis is performed to join the Roux-limb to the portion of the jejunum extending below the lower portion of the dissected stomach, often referred to as a enteroenterostomy. The enteroenterostomy often occurs approximately 75 centimeters distal to the gastroenterostomy.

Current minimally invasive techniques are difficult for surgeons to master, and have many additional drawbacks. For instance, a laparoscopically inserted circular stapler requires an incision in the intestines to perform its function. The incision increases chances of contamination of the abdomen with bowel contents, and requires closure.

Therefore, there exists in a gastric bypass operation a need to simplify the procedure, to reduce the number and size of laparoscopic ports opened into the human body, and to reduce the potential for abdominal leakage and contamination.

SUMMARY OF THE INVENTION

A method to perform a gastric bypass procedure on the digestive system, using surgical tools and anastomosis members inserted transorally, is disclosed. Two anastomosis members are placed transorally and passed into the distal small intestine. The small intestine is transected proximally to the two members to create a drainage loop and the Roux limb. An anastomosis instrument is inserted transorally to join the most distal anastomosis member to the drainage loop. The stomach is then transected to form a small gastric pouch. An anastomosis instrument then is inserted transorally to join the more proximal anastomosis member to the gastric pouch. The method reduces the number of laparoscopic ports, avoids a laparoscopic insertion of an anastomosis instrument into an enlarged surgical port, and eliminates the need for an enterotomy and an enterotomy closure. The anastomotic members within the digestive system can be distinguished to ensure proper rerouting of the digestive system.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
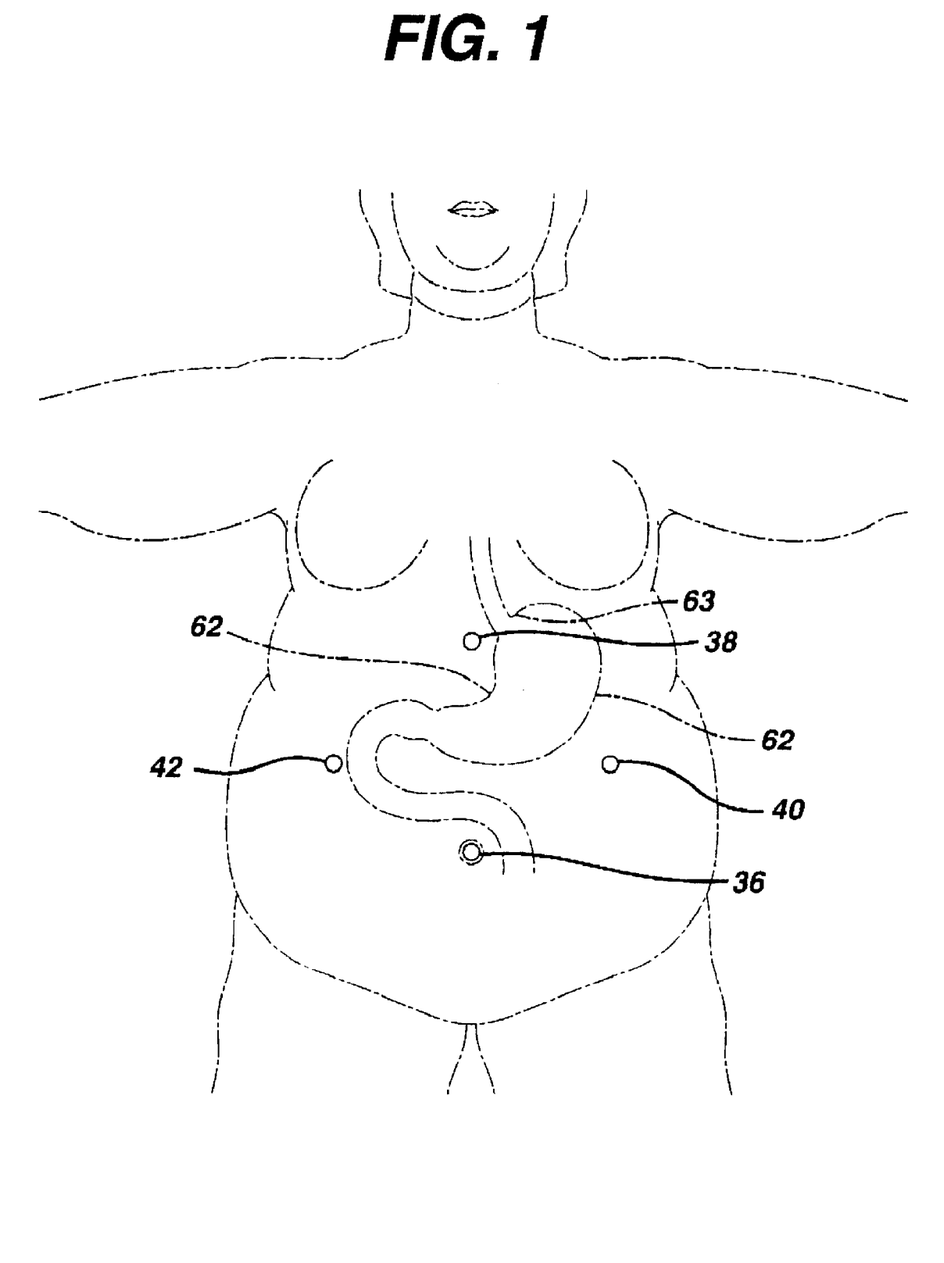
FIG. 1 is a view of the body showing an example of port placement in the patient.

FIG. 1 shows a possible placement of laparoscopic ports that may be used to practice the described method. A physician first insufflates the peritoneal cavity with insufflation gases that are introduced through a Veress needle inserted in the left upper quadrant on about the midclavicular line. Alternately, the physician may insufflate using an open technique for primary port placement. The abdominal cavity lining then distends under the pressure of the gas to provide enhanced access for surgical tools.

After insufflation, the physician can insert an umbilical port 36 for introduction of a laparoscopic camera (not shown). The physician also can insert trocars at the following locations: a sub-xiphoid port 38; a left upper quadrant port 40; and a right upper quadrant port 42. The ports allow access into the body by surgical tools.

The physician may choose to insert a liver retractor to lift the liver (not shown) and the upper anatomy for examination. Lifting the liver provides access to stomach 62 near the esophagogastric junction 63. Instruments inserted through the upper quadrant ports can retract stomach 62 inferiorly to gain better access to esophagogastric junction 63.

Figure 2:
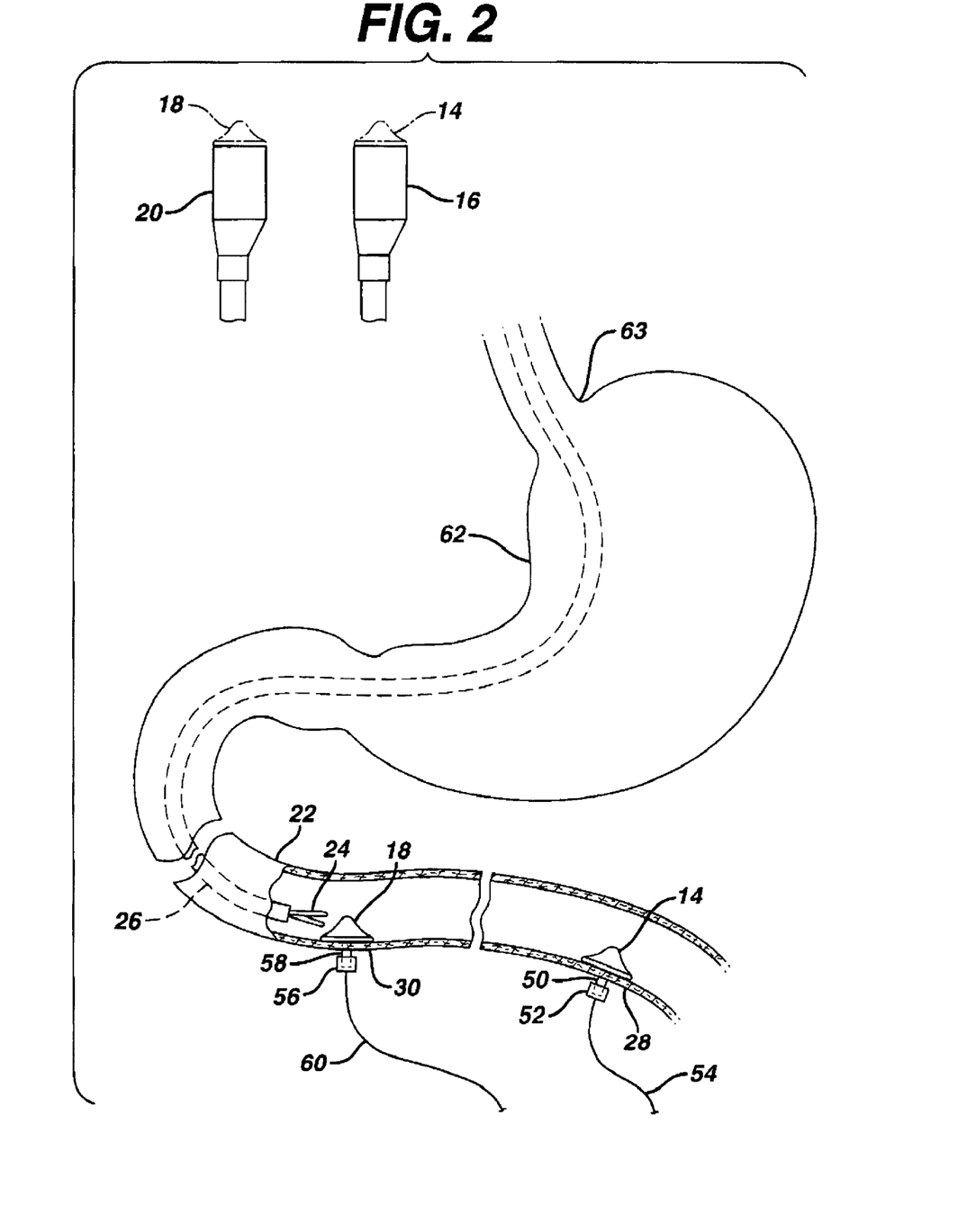
FIG. 2 is a view showing placement of anvils within the digestive system of a patient.

FIG. 2 shows a first anvil 14 and a second anvil 18 introduced within the portion of the intestine called the jejunum 22 of a surgical patient. To introduce first anvil 14, a physician first removes first anvil 14 from a first circular stapler 16. First circular stapler 16 may be, for example, a Circular Digital Loading Unit™ and part of an electrical powered and computer monitored system sold by Power Medical Interventions, Inc., in New Hope, Pa., as the SurgASSIST™ System. A grasper 24 is placed through the working channel of an endoscope 26 and first anvil 14 is placed at the end of grasper 24. The GF 140 gastroscope, sold by Olympus America in Melville, N.Y. may serve as an acceptable endoscope 26 for use in the procedure. Grasper 24 may be, for example, an endoscopic grasping forceps. The physician introduces endoscope 26 via a transoral approach through the mouth and esophagus of the patient. Grasping forceps inserted through one of the laparoscopic ports may assist in passing first anvil 14 through the pylorus. Endoscope 26 with first anvil 14 is moved to a position to place first anvil 14 to a distal location 28 of the surgeon's choice within jejunum 22 of the patient. Plicating the intestine on the outside of endoscope 26 may facilitate the maneuvering of first anvil 14. The physician views the procedure through a laparoscopic camera (not shown) introduced through umbilical port 36 (FIG. 1), and may accomplish precise positioning of first anvil 14 by grasping the outer portion of the digestive system containing first anvil 14 with grasping forceps placed through the one of the upper quadrant ports. A small enterotomy may then be made in the wall of jejunum 22, through which first stem 50 is externalized. After placement of first anvil 14, endoscope 26 with grasper 24 is removed through the mouth of the surgical patient. Distal location 28 is now in the vicinity of first anvil 14.

First anvil 14 now can be marked and made distinguishable. A first cap 52 is introduced into the body through a port of the physician's choice to attach to first stem 50. First cap 52 may provide a distinguishing characteristic, for example, color, to distinguish first anvil 14 from second anvil 18. To facilitate location of first anvil 14 within the body, first cap 52 may also provide a first filament 54 extending from first cap 52 extracorporially through right upper quadrant port 42. Alternatively, first filament 54 may be percutaneously anchored and extended through the skin of the patient. First filament 54 may have a distinguishing characteristic, such as color, to further distinguish first anvil 14 from second anvil 18, and may be a suture such as Prolene® suture, sold by Ethicon, Inc. in Sommerville, N.J. First filament 54 may also alternatively attach directly to first anvil 14.

Second anvil 18 is removed from second circular stapler 20. The physician has different alternatives regarding second circular stapler 20. Second circular stapler 20 may be, for example, a Circular Digital Loading Unit™ and part of an electrically powered and computer monitored system sold as the SurgASSIST™ System by Power Medical Interventions, Inc., in New Hope, Pa. The physician can use the loading unit to refill the reusable system with new staples. The physician can alternately use a second, completely disposable circular stapler 20 instead of a reload unit and a reusable system. Alternatively to using a second circular stapler 20, a physician could reuse first circular stapler 16 if first circular stapler 16 is reloadable with new staples and interchangeable with first anvil 14 and second anvil 18. Other choices may occur to the physician.

The physician then introduces second anvil 18. The physician attaches second anvil 18 to grasper 24 and transorally reintroduces endoscope 26 with grasper 24 and second anvil 18. Endoscope 26 with second anvil 18 is then maneuvered to a proximal location 30 of the physician's choice, proximal to distal location 28 within jejunum 22. As with placement of first anvil 14, placement of second anvil 18 may be facilitated by plicating the intestine on the outside of flexible endoscope 26. Proximal location 30 is in the vicinity of second anvil 18. The physician may make a small enterotomy at proximal location 30 to expose second stem 58 outside of jejunum 22. First anvil 14, or the distal anvil, and second anvil 18, or the proximal anvil, are now positioned within jejunum 22.

Second anvil 18 now can be marked and made distinguishable. A second cap 56 is introduced into the body through a port of the physician's choice to attach to second stem 58. Second cap 56 may also provide a distinguishing characteristic, for example, color, to distinguish first anvil 14 from second anvil 18. Second cap 56 may be, for example, blue in color, while first cap 52 may be, for example, red in color. Second cap 56 may also provide a second filament 60 extending from second cap 56 extracorporially through right upper quadrant port 42 or extending percutaneously through the skin of the patient. Second filament 60 may have a distinguishing characteristic, such as color, to further distinguish first anvil 14 from second anvil 18. Second filament 60 may also be a suture thread such as Prolene® suture, sold by Ethicon, Inc. in Sommerville, N.J., and may also have an alternate attachment directly to second anvil 18.

Figure 3:
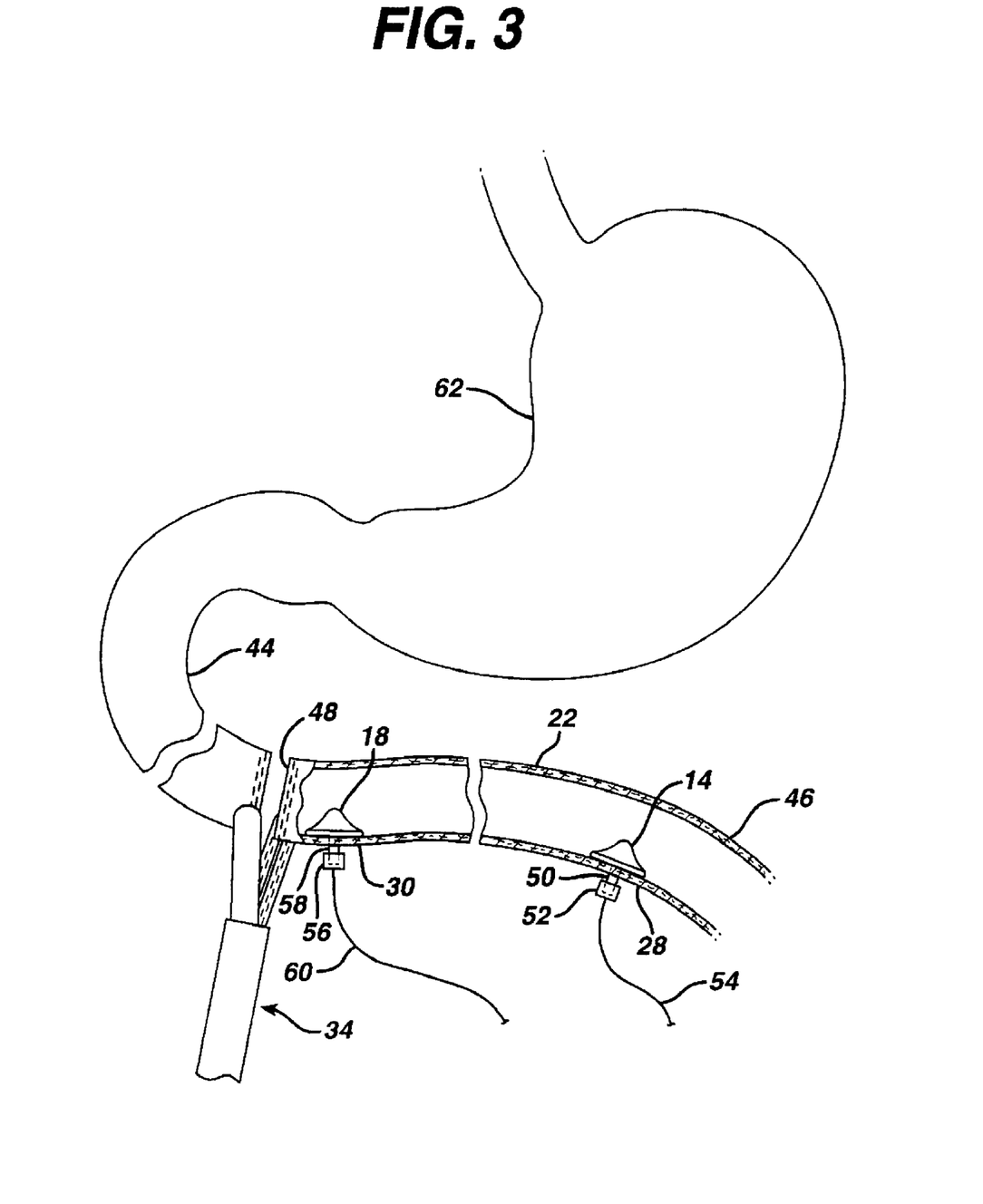
FIG. 3 is a view showing transection of a portion of the digestive system of a patient.

FIG. 3 shows the transection of jejunum 22. To perform the transection the physician can introduce laparoscopically, through right upper quadrant port 42, an endoscopic linear cutter 34. An endoscopic linear cutter 34, or a surgical cutter, transects jejunum 22 at a transection line 48 just proximal to proximal location 30, leaving a drainage loop 44 and a Roux limb 46. Endoscopic linear cutter 34 may be, for example, an Endopath ETS™ Endoscopic Linear Cutter, made by Ethicon EndoSurgery, in Cincinnati, Ohio.

Figure 4:
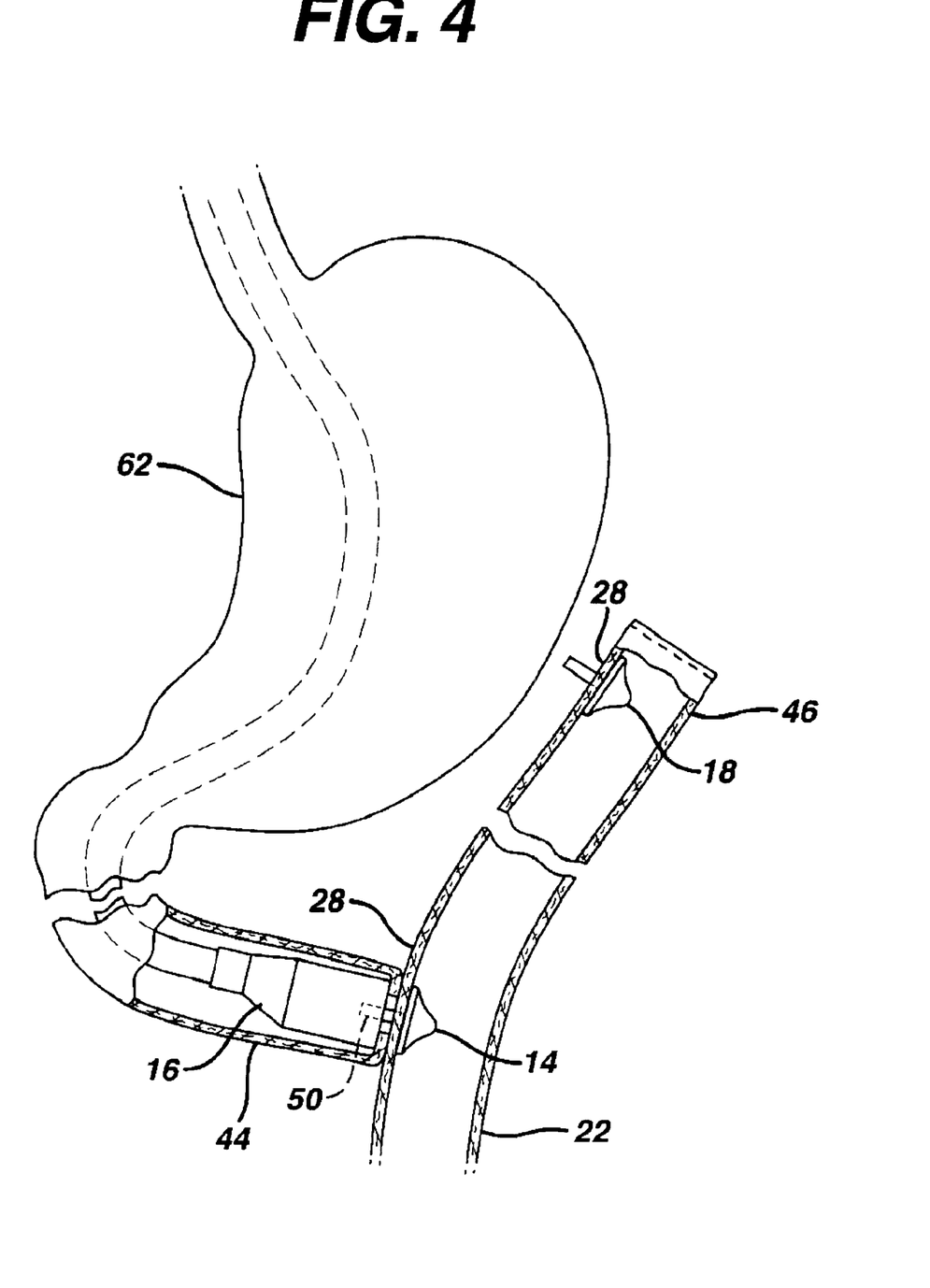
FIG. 4 is a view showing anastomosis of the drainage loop to the jejunum of a patient.

FIG. 4 illustrates a enteroenterostomy performed in the procedure. The physician passes first circular stapler 16 through the patient's mouth and esophagus into drainage loop 44. Grasping forceps may aid in passage of first circular stapler 16 through the pylorus. A small enterotomy is made in drainage loop 44 using, for example, a surgical blade, an ultrasonic device, or a radio-frequency current device. Distal location 28 and first anvil 14 are located using the distinguishing characteristic associated with first anvil 14. First cap 52, if used, may be removed. First anvil 14 is grasped using an endoscopic grasper inserted through an upper-quadrant port and manipulated into a position to attach to circular stapler 16. First stem 50 is attached to first circular stapler 16 and adjusted to the proper tissue compression. First circular stapler 16 is fired to place a circular array of staples to approximate the tissue of drainage loop 44 to the tissue of jejunum 22 in the area of distal location 28. First circular stapler 16 also cuts a circular opening to allow fluid to flow between drainage loop 44 and jejunum 22. Drainage loop 44 with the gastric segment and duodenum joins to jejunum 22 to provide drainage of pancreatic, biliary, and gastric secretions to jejunum 22. First circular stapler 16, with first anvil 14, is removed transorally from the patient.

First circular stapler 16 may be equipped with computer control. The physician can utilize computer control to control performance parameters of first circular stapler 16 such as, for example, staple height, cutting function, and stapling function. First circular stapler 16 may also be equipped with controls to permit remote tilting or steering of the distal end of first circular stapler 16 to allow access to regions that are difficult to reach.

Figure 5:
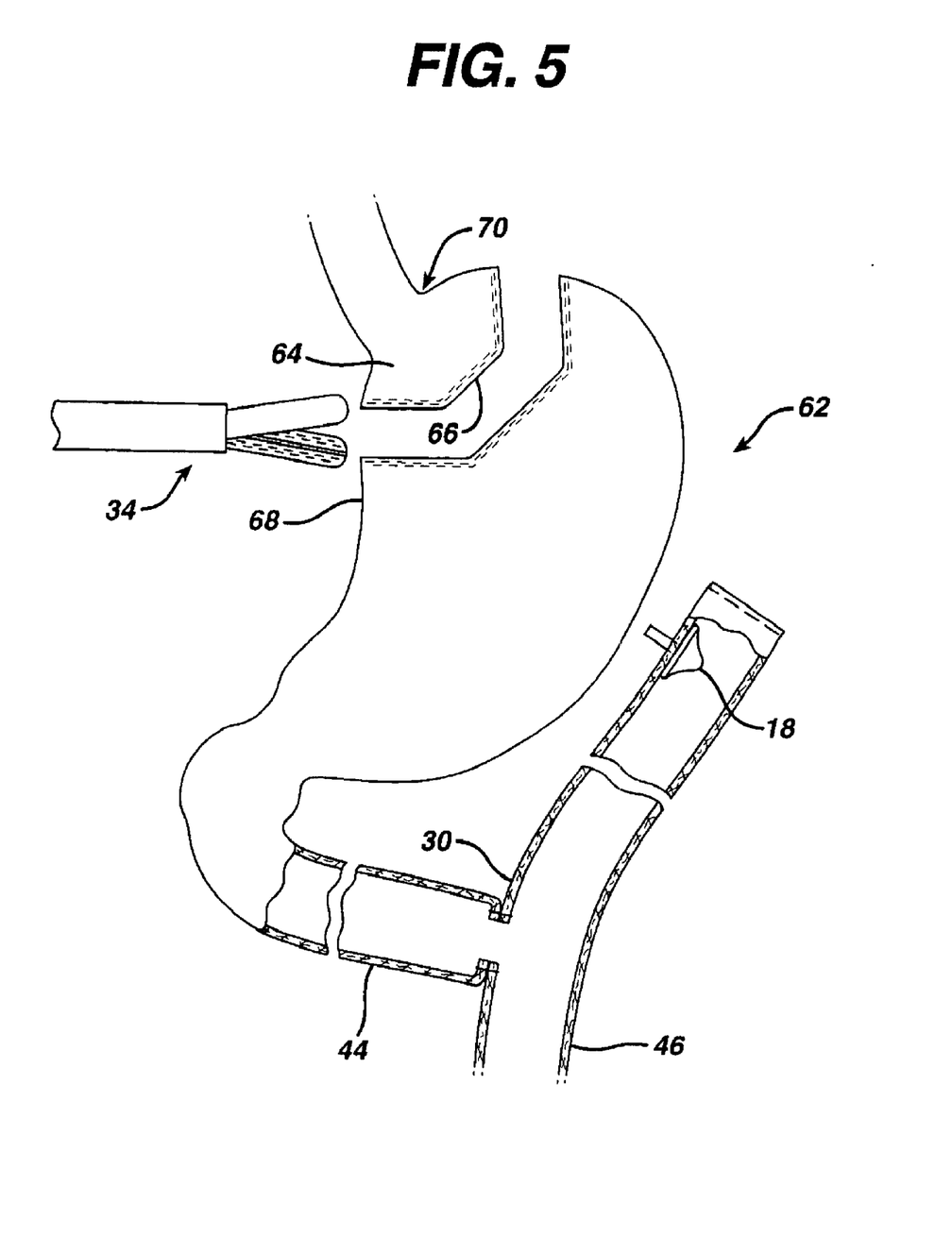
FIG. 5 is a view showing transection of the stomach.

FIG. 5 shows endoscopic linear cutter 34 applied to transect stomach 62. Successive applications of endoscopic linear cutter 34, starting at proximal lesser curvature 68 and proceeding along gastric transection line 66 to the angle of His 70 will divide stomach 62 to create gastric pouch 64. Staple lines placed by endoscopic linear cutter 34 may be overstitched at the preference of the physician to provide a serosal covering.

Figure 6:
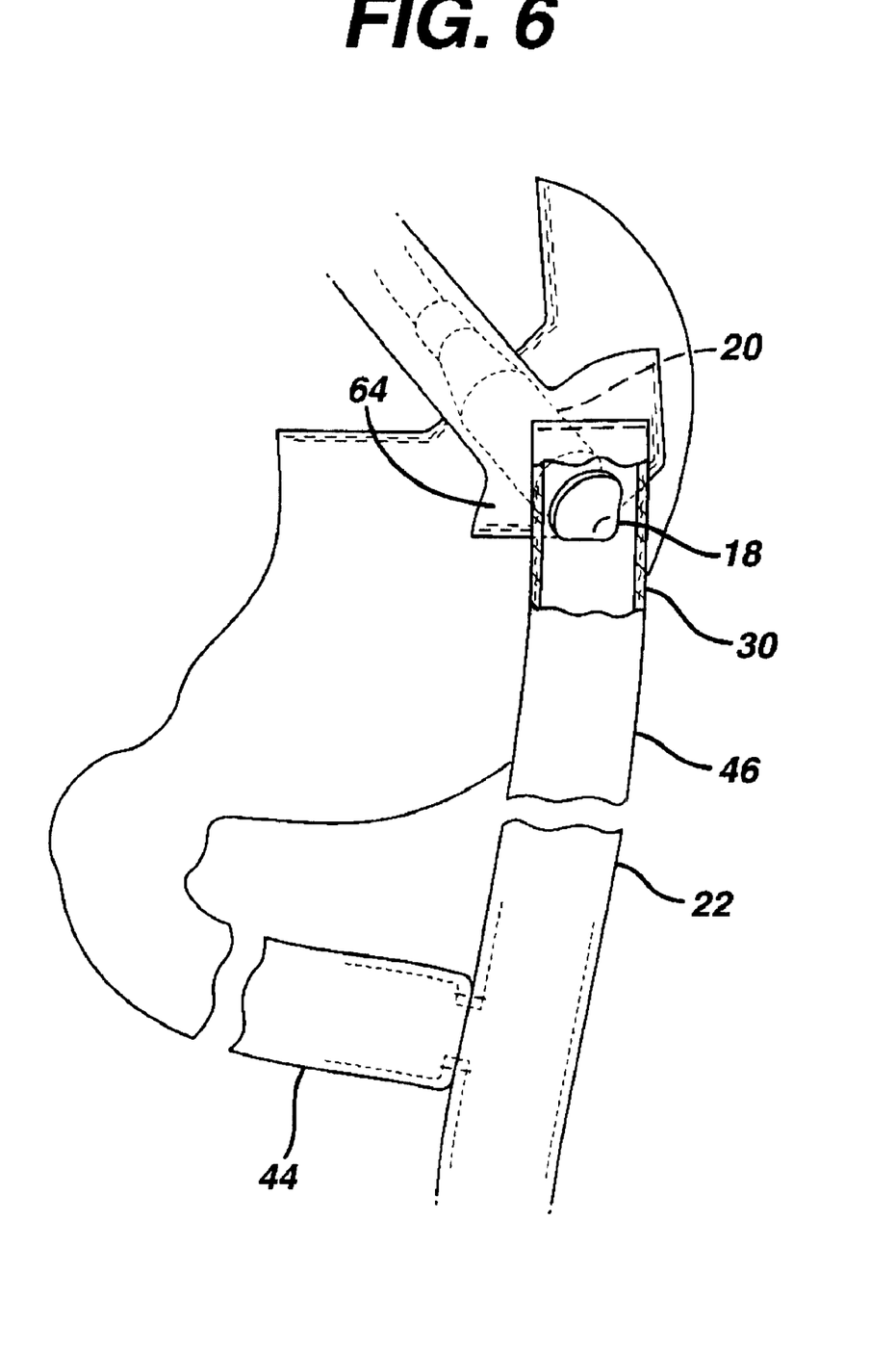
FIG. 6 is a view showing anastomosis of the roux limb to the gastric pouch.

FIG. 6 depicts joining of Roux limb 46 to gastric pouch 64 in a gastroenterostomy. Second circular stapler 20 is inserted through the mouth and esophagus of the patient into gastric pouch 64. The liver may be retracted once again using a liver retractor passed through one of the upper quadrant ports. An opening is created in gastric pouch 64 by, for example, use of a harmonic scalpel, a surgical blade, or a radio-frequency current device. The physician locates second anvil 18 and removes second cap 56 (FIG. 2) if second cap 56 were used. Using an endoscopic grasper the physician maneuvers second anvil 18 and Roux limb 46 up to gastric pouch 64. A window, called a retrogastric-retrocolic tunnel, may be created in the transverse mesocolon just lateral to the ligament of Trietz using scissors or a harmonic scalpel. Roux limb 46 can insert through the retrogastric-retrocolic tunnel to facilitate passage of Roux limb 46 to gastric pouch 64. Second anvil 18 carries proximal location 30 of Roux limb 46 to second circular stapler 20 where Roux limb 46 is anastomosed to gastric pouch 64. Second circular stapler 20 delivers a circular array of staples and makes a circular opening between gastric pouch 64 and Roux limb 46. Ingesta can pass from gastric pouch 64 to jejunum 22, avoiding the absorption of contents that would occur in drainage loop 44. Second circular stapler 20 and second anvil 18 are removed transorally from the body of the patient.

Second circular stapler 20 may be equipped with computer control. The physician can utilize computer control to control performance features of second circular stapler 20 such as, for example, staple height, cutting function, and stapling function. Second circular stapler 20 may also be equipped with controls to permit remote tilting or steering of the distal end of second circular stapler 20 to allow access to regions that are difficult to reach.

It will be recognized that equivalent methods may be substituted for the methods illustrated and described herein and that the described embodiment of the invention is not the only method that may be employed to implement the claimed invention.

Physicians may prefer to employ other types of surgery on the digestive system using an embodiment of the described intraluminal method. An embodiment described is utilized in a Roux-en-y gastric bypass procedure. Other types of gastric bypass procedures may include those in which the stomach is not divided by severing a portion of it. A portion of the stomach is instead separated from the rest by staple lines only, as in a gastroplasty. Other type of gastric bypass procedures may further include those in which the gastric pouch is formed from alternate portions of the stomach such as a portion along the lesser curvature, rather than along the fundus as previously described. Yet another type of gastric bypass procedure, the Fobi procedure, can utilize a restrictive band placed at the gastric pouch to inhibit the passage of food. As another example of an embodiment that can be used to implement the claimed invention, first and second anvils may be, for example, first and second anastomosis members inserted transorally. A physician introduces the first, or distal anastomosis member, transorally and advances the distal anastomosis member to the distal portion of the jejunum. The distal anastomosis member may at least partially penetrate the jejunum to secure its location. The second, or proximal member, is then introduced transorally and advanced to a proximal location of the jejunum, and may also at least partially penetrate the jejunum to secure its location. The proximal anastomosis member and the distal anastomosis member may be marked and made distinguishable from each other using, for example, color, geometry, fluorescence, or magnetic attraction. A surgical cutter introduced through a port or an incision on the patient's body may transect the jejunum proximal to the first anastomosis member. The surgical cutter can sever the jejunum along a transection line while stapling along the severed edges to control bleeding. The transected jejunum separates into the drainage loop, which is attached to the stomach, and the Roux limb, which comprises a distal portion of the jejunum.

An anastomosis instrument, such as a circular stapler, or an endoscope equipped with a device to maneuver the anastomosis members, is introduced transorally into the drainage loop. The anastomosis instrument engages the distal anastomosis member to join the drainage loop to the distal portion of the jejunum. After anastomosis, the distal anastomosis member may be removed, if necessary, transorally from the patient by utilizing the anastomosis instrument. Pancreatic, biliary, and gastric secretions may flow from the stomach to the distal portion of the jejunum.

A surgical cutter introduced through a port or an incision on the patient's body transects the stomach. Transection of the stomach forms the gastric pouch proximal to the drainage loop. The transection may include severing the stomach along a transection line and sealing the severed ends along either side of the transection line by stapling them.

An anastomosis instrument, such as a circular stapler, or an endoscope equipped with a device to maneuver the anastomosis members, is introduced transorally into the gastric pouch. The anastomosis instrument engages the proximal anastomosis member to join the gastric pouch to the proximal portion of the jejunum so that ingesta may flow from the gastric pouch to the jejunum. After anastomosis, the proximal anastomosis member may be removed, if necessary, transorally from the patient by utilizing the anastomosis instrument. The ingesta does not mix with pancreatic, biliary, and gastric secretions until it reaches a distal portion of the jejunum at the section anastomosed to the drainage loop. Mixing secretions and ingesta more distally in the digestive tract causes malabsorption, which helps weight loss.

Figure 7:
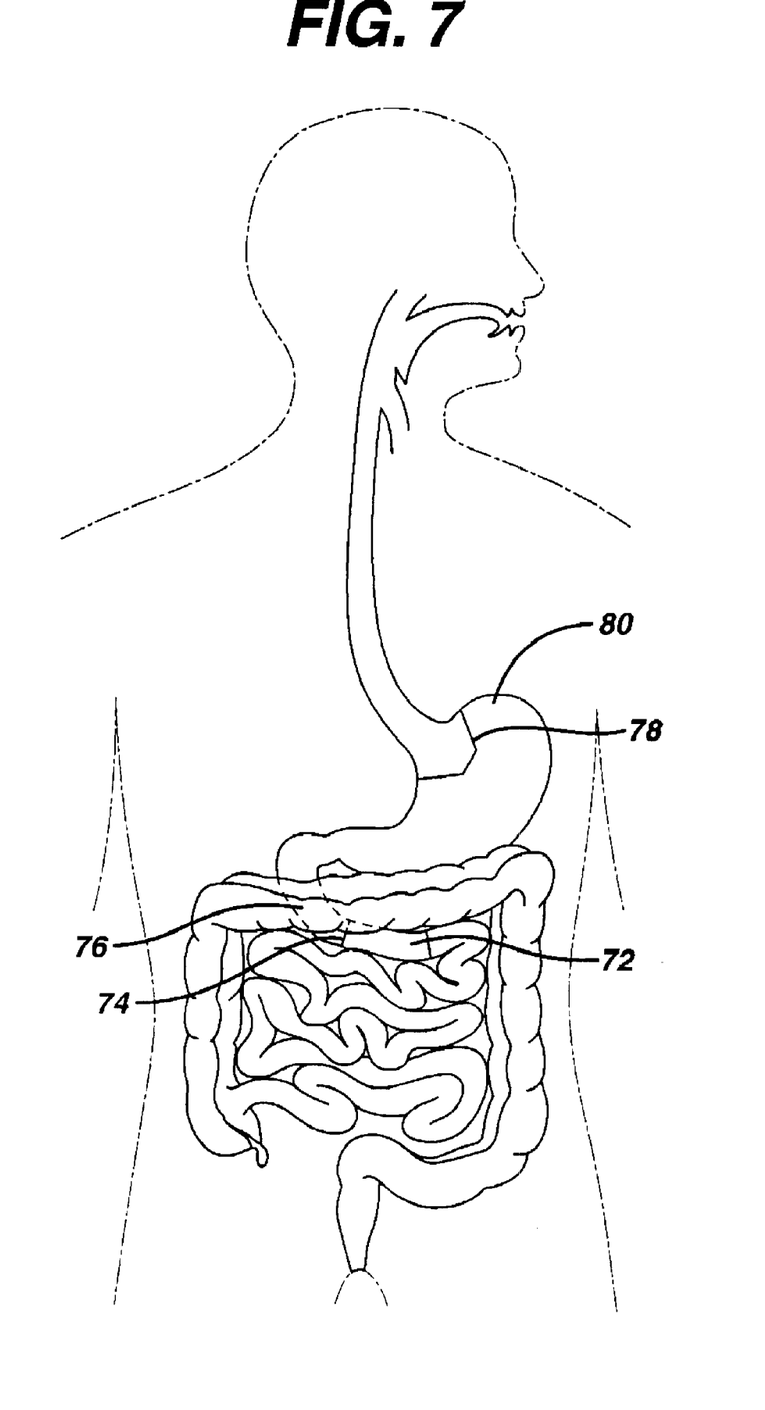
FIG. 7 is a diagrammatic view showing regions of placement of anastomosis members and regions of transection.

As another example of an embodiment that can be used to implement the claimed invention, a physician may elect to transect and join portions of the digestive system at any location of the physician's choice, illustrated by FIG. 7. A first anastomosis member and a second anastomosis member may be disposed at first portion 72 of the digestive system. The anastomosis members may be distinguished from each other in any manner including, for example, color, geometry, or fluorescence. The digestive system may be transected at first transection point 74, offset from the anastomosis members, creating a second portion 76 of the digestive system separate from first portion 72. First transection point 74 may be proximal to the most proximal anastomosis member. The most distal, or first, anastomosis member may then join second portion 76 of the system to an area of first portion 72 of the digestive system in the vicinity of the first anastomosis member. The digestive system is again transected at a second transection point 78, creating a third portion 80 of the digestive system. Second transection point 78 may be proximal of first transection point 74. The most proximal, or second, anastomosis device can be used to join third portion 80 to an area of first portion 72 of the digestive system in the vicinity of the second anastomosis member. The joined lumens of the digestive system allow digestive secretions and ingesta to pass through openings created by the anastomosis members.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for performing a gastric bypass procedure on a patient, the method comprising:
   a. introducing a distal anastomosis member transorally into a patient and advancing it to a distal location of the intestine;
   b. introducing a proximal anastomosis member transorally into a patient and advancing it to a proximal location of the intestine;
   c. transecting the intestine proximal to the proximal anastomosis member, thereby creating a drainage loop;
   d. introducing an anastomosis instrument transorally into a patient and into the drainage loop and creating an anastomosis between the drainage loop and the distal portion of the intestine by engaging the anastomosis instrument with the distal anastomosis member;
   e. transecting the stomach to create a gastric pouch proximal to the drainage loop; and
   f. introducing the anastomosis instrument transorally into a patient and into the gastric pouch and creating an anastomosis between the gastric pouch and the proximal portion of the intestine by engaging the anastomosis instrument with the proximal anastomosis member.

2. The method of claim 1 wherein the step of introducing a distal anastomosis member transorally into a patient and advancing it to a distal location of the intestine further comprises at least partially penetrating the intestine with the distal anastomosis member, and wherein the step of introducing a proximal anastomosis member transorally into a patient and advancing it to a proximal location of the intestine further comprises at least partially penetrating the intestine with the proximal anastomosis member.

3. The method of claim 1 wherein the step of transecting the intestine proximal to the proximal anastomosis member comprises severing the intestine along a transection line and sealing the intestine along either side of the transection line.

4. The method of claim 1 further including the step of removing the distal anstomosis member from the patient after creating the anastomosis between the drainage loop and the distal portion of the intestine.

5. The method of claim 1 wherein the step of transecting the stomach comprises severing the stomach along a transection line and sealing the stomach along either side of the transection line.

6. The method of claim 1 further including the step of removing the proximal anastomosis member from the patient after creating an anastomosis between the gastric pouch and the proximal portion of the intestine.

7. The method of claim 1 further including the step of distinguishing the proximal anastomosis member from the distal anastomosis member by providing a characteristic in one of the proximal anastomosis member and the distal anastomosis member that is different than the other of the proximal anastomosis member and the distal anastomosis member.

8. A method for performing a gastric bypass procedure on a patient, the method comprising:
   a. introducing a distal anvil transorally into a patient and advancing it to a distal location of the intestine;
   b. introducing a proximal anvil transorally into a patient and advancing it to a proximal location of the intestine;
   c. transecting the intestine proximal to the proximal anvil, thereby creating a drainage loop;
   d. introducing a circular stapler transorally into a patient and into the drainage loop and creating an anastomosis between the drainage loop and the distal portion of the intestine by attaching the stapler to the distal anvil and firing the stapler;
   e. transecting the stomach to create a gastric pouch proximal to the drainage loop; and
   f. introducing a circular stapler transorally into a patient and into the gastric pouch loop and creating an anastomosis between the gastric pouch and the proximal portion of the intestine by attaching the stapler to the proximal anvil and firing the stapler.

9. The method of claim 8 wherein the step of introducing a distal anvil transorally into a patient and advancing it to a distal location of the intestine further comprises at least partially penetrating the jejenum with the distal anvil, and wherein the step of introducing a proximal anvil transorally into a patient and advancing it to a proximal location of the intestine further comprises at least partially penetrating the jejenum with the proximal anvil.

10. The method of claim 8 wherein the step of transecting the intestine proximal to the proximal anastomosis member comprises severing the intestine along a transection line and sealing the intestine along either side of the transection line.

11. The method of claim 8 further including the step of removing the distal anvil from the patient after creating the anastomosis between the drainage loop and the distal portion of the intestine.

12. The method of claim 8 wherein the step of transecting the stomach comprises severing the stomach along a transection line and sealing the stomach along either side of the transection line.

13. The method of claim 8 further including the step of removing the proximal anvil from the patient after creating an anastomosis between the gastric pouch and the proximal portion of the intestine.

14. The method of claim 8 further including the step of distinguishing the proximal anvil from the distal anvil by providing a characteristic in one of the proximal anvil and the distal anvil that is different than the other of the proximal anvil and the distal anvil.

15. A method for performing a gastric bypass procedure on a patient, the method comprising:

a. introducing a distal anastomosis member transorally into a patient and advancing it to a distal location of the intestine;

b. introducing a proximal anastomosis member transorally into a patient and advancing it to a proximal location of the intestine;

c. accessing the interior of the patient through an incision and introducing a surgical cutter therethrough, and thereafter transecting the intestine proximal to the proximal anastomosis member with the surgical cutter, thereby creating a drainage loop;

d. introducing an anastomosis instrument transorally into a patient and into the drainage loop and creating an anastomosis between the drainage loop and the distal portion of the intestine by engaging the anastomosis instrument with the distal member;

e. accessing the interior of the patient through an incision and introducing a surgical cutter therethrough, and thereafter transecting the stomach with the surgical cutter to create a gastric pouch proximal to the drainage loop; and f. introducing an anastomosis instrument transorally into a patient and into the gastric pouch and creating an anastomosis between the gastric pouch and the proximal portion of the intestine by engaging the instrument with the proximal member.

16. The method of claim 15 wherein the step of introducing a distal anastomosis member transorally into a patient and advancing it to a distal location of the intestine further comprises at least partially penetrating the jejenum with the distal anastomosis member, and wherein the step of introducing a proximal anastomosis member transorally into a patient and advancing it to a proximal location of the intestine further comprises at least partially penetrating the jejenum with the proximal anastomosis member.

17. The method of claim 15 wherein the step of transecting the intestine proximal to the first member comprises severing the intestine along a transection line with the surgical cutter and stapling the intestine along either side of the transection line.

18. The method of claim 15 further including the step of removing the distal anstomosis member from the patient after creating the anastomosis between the drainage loop and the distal portion of the intestine.

19. The method of claim 15 wherein the step of transecting the stomach comprises severing the stomach along a transection line with the surgical cutter and stapling the stomach along either side of the transection line.

20. The method of claim 15 further including the step of removing the proximal anastomosis member from the patient after creating an anastomosis between the gastric pouch and the proximal portion of the intestine.

21. The method of claim 15 further including the step of distinguishing the proximal anastomosis member from the distal anastomosis member by providing a characteristic in one of the proximal anastomosis member and the distal anastomosis member that is different than the other of the proximal anastomosis member and the distal anastomosis member.

* * * * *